United States Patent
Mettler et al.

[11] Patent Number: 6,127,548
[45] Date of Patent: Oct. 3, 2000

[54] PROCESS FOR THE PREPARATION OF FORMYLIMIDAZOLES

[75] Inventors: Hanspeter Mettler, Visp; Paul Hanselmann, Brig-Glis, both of Switzerland

[73] Assignee: Lonza AG, Gampel/Valais, Switzerland

[21] Appl. No.: 09/335,757

[22] Filed: Jun. 18, 1999

[30] Foreign Application Priority Data

Jun. 18, 1999 [EP] European Pat. Off. ............... 98111174

[51] Int. Cl.$^7$ ..................... C07D 233/56; C07D 233/58; C07B 41/06
[52] U.S. Cl. .................. 548/333.5; 548/316.4; 548/318.5
[58] Field of Search .......................... 548/333.5

[56] References Cited

U.S. PATENT DOCUMENTS

| | | | |
|---|---|---|---|
| 3,812,189 | 5/1974 | English et al. ................. | 548/333.5 X |
| 4,924,000 | 5/1990 | Hesse et al. ..................... | 548/333.5 |
| 5,521,206 | 5/1996 | Muller et al. ..................... | 514/400 |
| 5,565,577 | 10/1996 | Mokhallalatz et al. ............ | 548/333.5 |
| 5,917,051 | 6/1999 | Heveling et al. ................. | 548/333.5 |

FOREIGN PATENT DOCUMENTS

| | | | |
|---|---|---|---|
| 0300324 | 1/1989 | European Pat. Off. ............. | 548/333.5 |
| 55-157570 | 12/1980 | Japan ................................ | 548/333.5 |
| 63-243076 | 10/1988 | Japan ................................ | 548/333.5 |
| 02-108670 | 4/1990 | Japan ................................ | 548/333.5 |
| 02-134369 | 5/1990 | Japan ................................ | 548/333.5 |
| 06-239837 | 8/1994 | Japan ................................ | 548/333.5 |
| 0685496 | 7/1995 | Switzerland ...................... | 548/333.5 |
| 92-20651 | 11/1992 | WIPO . | |

*Primary Examiner*—Floyd D. Higel
*Attorney, Agent, or Firm*—Fisher, Christen & Sabol

[57] ABSTRACT

A process for the preparation of formylimidazoles of the general formula:

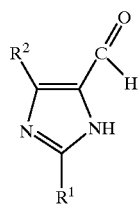

I or its tautomers, in which $R^1$ is hydrogen or alkyl, and $R^2$ is hydrogen, halogen or alkyl. In a first stage, an imidazole derivative of the general formula:

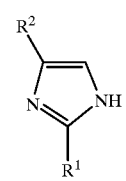

II or its tautomers, in which $R^1$ and $R^2$ are as defined above, is converted, by introducing an amino protective group, into an imidazole derivative of the general formula:

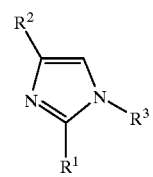

III or its tautomers, in which $R^3$ is an amino protective group. Such derivative is formylated in a second stage in the presence of an organometallic compound and a suitable electrophile to give an imidazole derivative of the general formula:

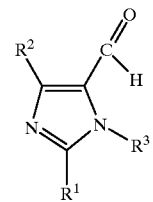

IV or its tautomers, in which $R^1$, $R^2$ and $R^3$ are as defined above. Then, in a third stage, the end product of the formula I is obtained by cleaving off the amino protective group.

19 Claims, No Drawings

PROCESS FOR THE PREPARATION OF FORMYLIMIDAZOLES

BACKGROUND OF THE INVENTION

1. Field of the Invention

The invention relates to a novel process for the preparation of formylimidazoles of the general formula:

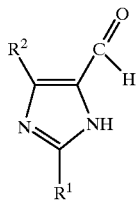

I or its tautomers, in which $R^1$ is hydrogen or alkyl, and $R^2$ is hydrogen, halogen or alkyl.

2. Background Art

Formylimidazoles are important intermediates for the preparation of pharmaceutical active ingredients, such as, for diuretics or antihypertensives (WO 92/20651).

A process for the preparation of formylimidazoles is described, for example, in Swiss Patent No. 685,496. In this process, hydroxymethylimidazoles are oxidized by catalytic oxidation in the presence of noble-metal catalysts, such as, platinum-bismuth, platinum black, platinum or palladium on activated carbon, while passing in oxygen to give the formylimidazoles. Disadvantages of such process are long reaction times and the formation of by-products.

BROAD DESCRIPTION OF THE INVENTION

The object of the present invention is, therefore, to provide a more economical process for the preparation of formylimidazoles, with which the products are isolated in high purity. This object is achieved by the process according to the invention.

Alkyl is defined below as a straight-chain or branched alkyl group. Alkyl is expediently $C_{1-6}$-alkyl, such as, methyl, ethyl, propyl, isopropyl, butyl, isobutyl, tert-butyl, pentyl and its isomers, and hexyl and its isomers. Alkyl is preferably butyl.

Halogen is defined below as F, Cl, Br and I. Halogen is preferably Cl.

The term "tautomers" means that the compounds differ merely with respect to the position of a movable group and the position of a double bond. Accordingly, tautomeric compounds of the general formula I can be 4- or 5-formylimidazoles, such as, 2-alkyl-4-formyl-5-alkylimidazoles, 4-formyl-5-alkylimidazoles, 4-formyl-5-haloimidazoles, 2-alkyl-4-formyl-5-haloimidazoles, 2-alkyl-4-alkyl-5-formylimidazoles, 2-alkyl-4-halo-5-formylimidazoles, 4-alkyl-5-formylimidazoles and 4-halo-5-formylimidazoles. Tautomeric compounds of the general formulae II and III are expediently the corresponding non-formylated compounds, and tautomeric compounds of the general formula IV are the corresponding formylated N-protected compounds. Preferred compounds of the general formula I are 2-butyl-4-formylimidazole and 2-butyl-5-formylimidazole.

In the first stage of the process according to the invention, an imidazole derivative of the general formula:

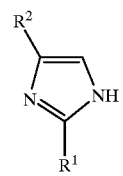

II or its tautomers, in which $R^1$ and $R^2$ are as defined above, is converted, by introducing an amino protective group, into an imidazole derivative of the general formula:

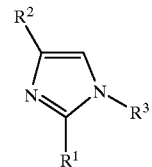

III and its tautomers, in which $R^3$ is an aminoprotective group.

The imidazole derivatives of the general formula II (starting materials), such as, 2-butylimidazole, are commercially available compounds, or can be prepared in a known manner as in U.S. Pat. No. 2,847,417 or as in J. L. Hughey, Synth., (1980), 489.

The amino protective groups can be those groups customary to the person skilled in the art, such as, dialkylaminomethyl, dialkylaminosulfonyl, alkylsulfonyl, alkoxymethyl, 1-alkoxyethyl, dialkoxymethyl, aryloxycarbonyl, aliphatic oxycarbonyl, piperidinomethyl and toluenesulfonyl. The dialkylaminomethyl can, for example, be dimethylaminomethyl, dimethylaminoethyl or dimethylaminopropyl. The dialkylaminosulfonyl can, for example, be dimethylaminosulfonyl or diethylaminosulfonyl. The alkylsulfonyl can be methyl-, ethyl-, propyl- or butylsulfonyl. The alkoxymethyl can, for example, be methoxymethyl, ethoxymethyl or propoxymethyl, and the dialkoxymethyl can be dimethoxymethyl, diethoxymethyl or dipropoxymethyl. Examples of 1-alkoxyethyl are 1-methoxyethyl, 1-ethoxyethyl and 1-propoxyethyl. The aryloxycarbonyl can, for example, be phenyloxycarbonyl. The aliphatic oxycarbonyl can be Z (benzyloxycarbonyl), BOC (tert-butoxycarbonyl) or FMOC (fluorenylmethoxycarbonyl). Preferred amino protective groups are piperidinomethyl, dialkylaminomethyl or dialkyaminosulfonyl.

As the person skilled in the art is aware, these amino protective groups are introduced using the corresponding protective group reagents. Protective groups reagents which can be used are dimethylamine/formaldehyde, piperidine/formaldehyde, bis(dimethylamino)methane, N,N-dimethylsulfamoyl chloride, orthoformate, BOC-Cl, Z-Cl, chloromethyl ethyl ether or dimethoxymethane.

As the person skilled in the art is aware, the choice of reaction temperature, the choice of solvent and the choice of pH are dependent on the amino protective group to be introduced and can be found in the corresponding specialist literature, such as, Houben Weyl, Methoden der organischen Chemie [Methods In Organic Chemistry], Volume 15 (1–2), Thieme Verlag Stuttgart, 1974.

If the preferred amino protective groups piperidinomethyl and dialkylaminomethyl (preparation of piperidinomethyl- and dialkylaminomethylimidazole from the corresponding amine and formaldehyde) are used, the reaction in the first stage is expediently carried out at a temperature of from 0° to 100° C., preferably at a temperature of from 15° to 50° C. The pH is expediently at a pH of from 0 to 8, preferably from 3 to 6. Suitable solvents are then water, polar protic or aprotic solvents such as tetrahydrofuran, methylene chloride and acetone, lower alcohols such as methanol, ethanol and propanol or mixtures thereof with water. The solvent is preferably water.

If, for example, dialkylaminomethylimidazole is prepared from the corresponding bis(dialkylamino)methane, the reaction is expediently carried out at a temperature of from 20° to 100° C., preferably at a temperature of from 60° to 90° C. Solvents which can then be used are polar aprotic ones, such as tetrahydrofuran, dioxane, dimethoxymethane, dimethylformamide, dimethyl sulfoxide, acetonitrile or methylene chloride.

If the preferred amino protective group dialkylaminosulfonyl (preparation of dialkylaminosulfonylimidazole from dialkylsulfamoyl chloride or sulfuryldiimidazole and sulfuryl chloride) is used, the reaction is expediently carried out at a temperature of from 0° to 60° C., preferably at a temperature of from 20° to 40° C. This reaction is expediently carried out in the presence of a base. The base can be a trialkylamine such as triethylamine, an alkali metal or alkaline earth metal carbonate such as sodium or potassium carbonate, an alkali metal or alkaline earth metal hydroxide such as sodium or potassium hydroxide, or the corresponding imidazole. If, for example, the corresponding imidazole is used as the base, it is used in excess. If one or the other bases listed is used, from 1 to 2 equivalents are expediently used. Preferably, from 1 to 1.2 equivalents of a trialkylamine are used as the base. The solvent can be a polar aprotic one, such as, tetrahydrofuran, dioxane, dimethoxymethane, dimethylformamide, dimethyl sulfoxide, acetonitrile and methylene chloride.

In the second process stage, the imidazole derivative of the general formula III, is formylated in the presence of an organometallic compound and a suitable electrophile to give an imidazole derivative of the general formula:

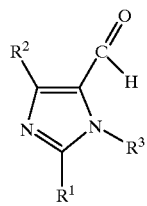

IV or its tautomers, in which $R^1$, $R^2$ and $R^3$ are as defined above.

Possible organometallic compounds are alkyl-metal compounds in which alkyl is defined as already described, such as, alkyl (alkali metal) compounds, alkylaluminum or alkylmagnesium compounds or compounds such as alkalimetal alkylamides. Suitable alkyl (alkali metal) compounds are alkyllithium, alkylsodium and alkypotassium. Suitable alkyllithium compounds are methyl-, ethyl-, propyl-, or butyllithium, suitable alkylsodium compounds are methyl-, ethyl-, propyl- or butylsodium, and suitable alkylpotassium compounds are methyl-, ethyl-, propyl- or butylpotassium. The alkali metal alkylamide can, for example, be lithium diisopropylamide.

The elecrophiles are compounds with a formyl leaving group, such as, N,N-dialkylformamide or alkyl formates. The N,N-dialkylformamide can be N,N-dimethylformamide, N,N-diethylformamide, N,N-dipropylformamide or N,N-dibutylformamide. Suitable alkylformates are methyl, ethyl, propyl or butyl formate. In particular, the electrophile is methyl formate.

The formylation in the second stage is expediently carried out at a temperature of from −100° to 50° C., preferably at a temperature of from −70° to 20° C. Suitable solvents for the second stage are aprotic solvents such as diethyl ether, tetrahydrofuran, methylene chloride and hexane.

In the third stage, the imidazole derivative of the general formula IV is converted into the end product of the general formula I by cleaving off the amino protective group.

The amino protective group is cleaved off in a manner customary to the person skilled in the art, such as, by adding an organic acid such as trifluoroacetic acid or a mineral acid such as hydrochloric acid, sulfuric acid or phosphoric acid, optionally in the presence of one of the organometallic compounds described above. Depending on the amino protective group, it is also possible to use a strong base such as sodium hydroxide. The amino protective group is preferably cleaved off by adding a mineral acid.

As the person skilled in the art is aware, the choice of reaction temperature and the choice of solvent are dependent on the amino protective group to be cleaved off and can, for example, also be found in Houben Weyl, ibid. If, for example, the amino protective group dialkylaminomethyl, described above as preferred, is cleaved off, the cleaving-off is carried out at a temperature of from 0° to 100° C., preferably at a temperature of from 20° to 50° C., and at a pH of from 0 to 7, preferably from 2 to 5. This cleaving-off expediently takes place in an aqueous or organic/aqueous medium. The cleaving-off preferably takes place by adding an organic acid or a mineral acid.

The cleaving-off of sulfonyl protective groups can take place at temperatures of from 0° to 100° C., preferably from 20° to 50° C., in the aqueous or organic/aqueous medium. This cleaving-off expediently takes place under strongly acidic (pH greater than 11) conditions. The pH is expediently adjusted either by adding an organic acid or a mineral acid or by adding a strong base such as sodium hydroxide.

The invention also relates to the compounds, not yet described in the literature, of the general formula:

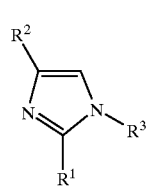

III or its tautomers, in which $R^1$ is alkyl, $R^2$ is hydrogen, and $R^3$ is an amino protective group, except for 2-methyl-3-dimethylaminomethylimidazole and 2-methyl-3-piperidinomethylimidazole and the compounds, not yet described in the literature, of the general formula:

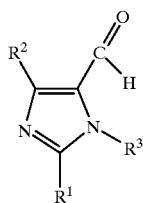

or its tautomers, in which $R^1$ is alkyl, $R^2$ is hydrogen, and $R^3$ is an amino-protective group.

Preferred novel compounds of the general formula III are 2-butyl-3-dimethylaminomethylimidazole, 2-ethyl-3-dimethylaminomethylimidazole, 2-propyl-3-dimethylaminomethylimidazole, 2-ethyl-3-piperidinomethylimidazole, 2-propyl-3-piperidinomethylimidazole, 2-butyl-3-piperidinomethylimidazole, 1,1-sulfuryldi-2-methylimidazole, 1,1-sulfuryldi-2-ethylimidazole, 1,1-sulfuryldi-2-propylimidazole, 1,1-sulfuryldi-2-butylimidazole, 2-methyl-3-dimethylaminosulfonylimidazole, 2-ethyl-3-dimethylaminosulfonylimidazole, 2-propyl-3-dimethylaminosulfonylimidazole and 2-butyl-3-diemethylaminosulfonylimidazole.

Preferred compounds of the general formula IV are 2-methyl-3-dimethylaminosulfonimidazole-4-carbaldehyde, 2-ethyl-3-dimethylaminosulfonimidazole-4-carbaldehyde, 2-propyl-3-dimethylaminosulfonimidazole-4-carbaldehyde, 2-butyl-3-dimethylaminosulfonimidazole-4-carbaldehyde, 2-methyl-3-dimethylaminomethylimdazole-4-carbaldehyde, 2-ethyl-3-dimethylaminomethylimdazole-4-carbaldehyde, 2-propyl-3-dimethylaminomethylimdazole-4-carbaldehyde, 2-butyl-3-dimethylaminomethylimdazole-4-carbaldehyde, 2-methyl-3-piperid inomethylimidazole-4-carbaldehyde, 2-ethyl-3-piperidinomethylimidazole-4-carbaldehyde, 2-propyl-3-piperidinomethylimidazole-4-carbaldehyde and 2-butyl-3-piperidinomethylimidazole-4-carbaldehyde.

DETAILED DESCRIPTION OF THE INVENTION

EXAMPLE 1

Preparation of 2-butyl-3-dimethylaminomethylimidazole (a) 2.48 g of butylimidazole was introduced into 4 ml of water, 1.66 g of dimethylamine hydrochloride was added and, with slight cooling, concentrated hydrochloric acid of pH 9.0 was added to adjust the pH to 4.9. 1.82 g of formalin (36 percent formaldehyde in water) was added, and the mixture was stirred for 72 hours at room temperature. It was rendered basic using 30 percent NaOH and extracted with ethyl acetate, and the organic phase was concentrated by evaporation to give 2.69 g of product as a yellow oil. The yield was 74 percent.

(b) 12.4 g of butylimidazole and 20.4 g of bis-(dimethylamino)methane were refluxed in 100 ml of tetrahydrofuran for 24 hours. The solvent was evaporated to give 18.64 g of product. The yield was quantitative. Other data concerning the product was:

| $^1$H NMR (CDCl$_3$): | |
|---|---|
| 6.94 ppm | (s, 1H) |
| 6.87 ppm | (s, 1H) |
| 4.45 ppm | (s, 2H) |
| 2.70 ppm | (t, 2H) |
| 2.26 ppm | (s, 6H) |
| 1.71–1.80 ppm | (m, 2H) |
| 1.38–1.46 ppm | (m, 2H) |
| 0.94 ppm | (t, 3H) |

EXAMPLE 2

2-Butyl-3-piperidinomethylimidazole 18.6 g of butylimidazole and 12.8 g of piperidine were introduced into 45 ml of water, and, with slight cooling, 30 g of concentrated hydrochloric acid was added. 15 g of formalin (36 percent formaldehyde in water) was added, and the mixture was stirred for 44 hours at room temperature. The mixture was rendered basic using 30 percent NaOH and extracted with ethyl acetate, and the organic phase was concentrated by evaporation to give 33.6 g of product as a yellow oil. The yield was quantitative. Other data concerning the product was:

| $^1$H NMR (CDCl$_3$): | |
|---|---|
| 7.00 ppm | (s, 1H) |
| 6.72 ppm | (s, 1H) |
| 4.52 ppm | (s, 2H) |
| 2.63 ppm | (t, 2H) |
| 2.35–2.40 ppm | (m, 4H) |
| 1.59–1.68 ppm | (m, 2H) |
| 1.42–1.50 ppm | (m, 4H) |
| 1.28–1.38 ppm | (m, 4H) |
| 0.89 ppm | (s, 3H) |

EXAMPLE 3

2-Butyl-3-dimethylaminosulfonylimidazole 12.4 g of butylimidazole and 13.3 g of N,N-dimethylsulfamoyl chloride were introduced into 200 ml of methylene chloride, and 9.7 g of triethylamine was added at room temperature. The mixture was stirred for 20 hours at room temperature and for 2 hours at 40° C., 200 ml of water was added and the phases were separated. The organic phase was washed with water, dried with Na$_2$SO$_4$ and concentrated by evaporation to give 22.2 g of product in the form of a red oil. The yield was 96 percent. Other data concerning the product was:

| $^1$H NMR (CDCl$_3$): | |
|---|---|
| 7.20 ppm | (s, 1H) |
| 6.94 ppm | (s, 1H) |
| 2.93 ppm | (t, 2H) |
| 2.88 ppm | (s, 6H) |
| 1.78–1.85 ppm | (m, 2H) |
| 1.39–1.48 ppm | (m, 2H) |
| 0.97 ppm | (t, 3H) |

EXAMPLE 4

2-Butyl-3-dimethylaminosulfonylim idazole4-carbaldehyde 1.25 g of 2-butyl-3-dimethylaminosulfonylimidazole was dissolved in 25 ml of tetrahydrofuran and cooled to −70° C., and 3.3 ml of n-butyllithium, 1.6 n in hexane, was added. After 1 hour, 0.64 ml of methyl formate was added, and the mixture was heated to room temperature and stirred for 17 hours at this temperature. The mixture was then concentrated, methylene chloride/water was added and the mixture was neutralized by adding 10 percent strength sulfuric acid. The organic phase was dried with Na$_2$SO$_4$ and concentrated by evaporation to give 1.35 g of crude product in the form of a yellow oil, which was purified by chromatography over methylene chloride/methanol/hexane 90:5:5 to give 0.99 g of product. The yield was 76 percent. Other data concerning the roduct was:

| $^1$H NMR (CDCl$_3$): | |
|---|---|
| 10.01 ppm | (s, 1H) |
| 7.76 ppm | (s, 1H) |
| 3.71–3.77 ppm | (m, 1H) |
| 3.00–3.02 ppm | (m, 1H) |
| 2.90 ppm | (s, 6H) |
| 1.80–1.88 ppm | (m, 2H) |
| 1.39–1.48 ppm | (m, 2H) |
| 1.92–1.99 ppm | (m, 3H) |

EXAMPLE 5

2-Butyl-3H-imidazole-4-carbaldehyde (a) 0.53 g of 2-butyl-3-dimethylaminosulfonylimidazole-4-carbaldehyde was stirred into 20 ml of 1 n hydrochloric acid for 20 hours at room temperature. Saturated NaHCO$_3$ solution was added to neutralize the solution, the product was extracted with ethyl acetate, and the extract was evaporated to give 0.33 g of crude product. The yield was quantitative.

(b) 1 g of 2-butyl-3-dimethylaminomethylimidazole was dissolved in 25 ml of tetrahydrofuran and cooled to −70° C., and 3.9 ml of n-butyllithium, 1.6 n in hexane, was added. After 1 hour, 0.73 g of N,N-dimethylformamide was added, and the mixture was warmed to room temperature and stirred for 17 hours at this temperature. 25 ml of 1 n hydrochloric acid was then added. The mixture was stirred for 15 minutes, some of the solvent was distilled off under reduced pressure, and the mixture was stirred for 1 hour at 50° C., neutralized with sodium bicarbonate and extracted with methylene chloride. The extract was evaporated to give 0.84 g of crude product in the form of an oil. The yield was quantitative.

What is claimed is:

1. A process for the preparation of a formylimidazole of formula:

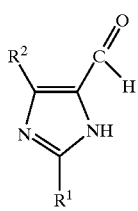

I or tautomers thereof, in which R$^1$ is hydrogen or alkyl, and R$^2$ is hydrogen, halogen or alkyl, comprising, in a first stage, converting an imidazole compound of formula:

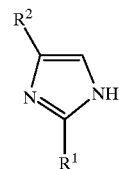

II or tautomer thereof, in which R$^1$ and R$^2$ are as defined above, by introducing an amino protective group into the imidazole compound of formula II to produce an imidazole compound of formula:

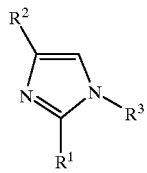

III in which R$^3$ is an amino protective group, whereby the conversion of the starting compound of the formula II into its N-protective derivative of the formula III is carried out by reacting the 3-amino group of the compound of the formula II with a corresponding protective group reagent, in a second stage, reacting the imidazole compound of formula III with a formulating reagent in the presence of an organometallic compound and an electrophile having a formyl leaving group to produce an imidazole compound of formula:

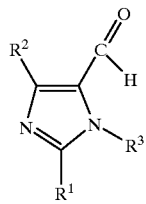

IV in which R$^1$, R$^2$, and R$^3$ are as defined above, and then, in a third stage, cleaving the amino protective group from the imidazole compound of formula IV by adding an acid or a strong base to produce the formylimidazole of formula I.

2. The process according to claim 1 wherein the conversion in the first stage is carried out in water or in a polar protic or polar aprotic solvent.

3. The process according to claim 2 wherein the amino protective group is dialkylaminosulfonyl, dialkylaminomethyl or piperidinomethyl.

4. The process according to claim 3 wherein the formylation in the second stage is conducted in an aprotic solvent.

5. The process according to claim 4 wherein the organometallic compound used in the second stage is an alkylmetal compound.

6. The process according to claim 5 wherein the alkylmetal compound is an alkyl(alkali metal) compound.

7. The process according to claim 1 wherein the amino protective group is dialkylaminosulfonyl, dialkylaminomethyl or piperidinomethyl.

8. The process according to claim 1 wherein the formylation in the second stage is carried out in an aprotic solvent.

9. The process according to claim 1 wherein the organometallic compound used in the second stage is an alkylmetal compound.

10. The process according to claim 9 wherein the alkyl-metal compound is an alkyl(alkali metal) compound.

11. The process according to claim 1, wherein the conversion in the first stage is conducted at a temperature of 0° to 100° C. and at a pH of 0 to 8 when the amino protective group is piperidinomethyl or dialkylaminomethyl.

12. The process according to claim 1 wherein the conversion in the first stage is conducted at a temperature of 20° to 100° C. when the amino protective group is dialkylaminomethyl.

13. The process according to claim 1 wherein the conversion in the first stage is conducted at a temperature of from 0° to 60° C. when the amino protective group is dialkylaminosulfonyl.

14. The process according to claim 1 wherein the formylating in the second stage is conducted at a temperature of −100° to 50° C.

15. The process according to claim 1 wherein the formyl leaving group is an N,N-dialkylformamide or an alkyl formate.

16. The process according to claim 1 wherein the cleaving in the third step is conducted using an organic acid, a mineral acid, or sodium hydroxide.

17. The process according to claim 1 wherein the cleaving in the third step is conducted at a temperature of 0° to 100° C. and at a pH of 0 to 7 when the amino protective group is dialkylaminomethyl.

18. The process according to claim 1, wherein the cleaving in the third step is conducted at a temperature of 0° to 100° C. when the amino protective group is a sulfonyl protective group.

19. A process for the preparation of a formylimidazole of formula:

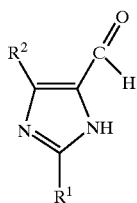

I or tautomers thereof, in which $R^1$ is hydrogen or alkyl, and $R^2$ is hydrogen, halogen or alkyl, comprising, in a first stage, converting an imidazole compound of formula:

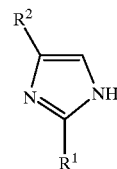

II or tautomer thereof, in which $R^1$ and $R^2$ are as defined above, by introducing an amino protective group into the imidazole compound of formula II in a suitable solvent at a temperature and a pH effective to achieve said conversion, to produce an imidazole compound of formula:

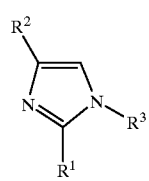

III in which $R^3$ is an amino protective group, whereby the conversion of the starting compound of the formula II into its N-protective derivative of the formula III is carried out by reacting the 3-amino group of the compound of the formula II with a corresponding protective group reagent, in a second stage, reacting the imidazole compound of formula III with a formylating reagent in the presence of an organometallic compound and an electrophile having a formyl leaving group in a suitable solvent at a temperature effective to achieve said formylation, to produce an imidazole compound of formula:

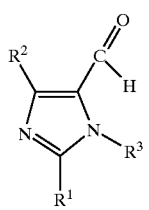

IV in which $R^1$, $R^2$, and $R^3$ are as defined above, and then, in a third stage, cleaving the amino protective group from the imidazole compound of formula IV by adding an acid or a strong base in a suitable solvent at a temperature effective to achieve cleaving, to produce the formylimidazole of formula I.

* * * * *